US009066987B2

(12) United States Patent  
Bettles et al.

(10) Patent No.: US 9,066,987 B2  
(45) Date of Patent: Jun. 30, 2015

(54) FLEXIBLE ULTRAVIOLET DEVICE

(71) Applicant: Sensor Electronic Technology, Inc., Columbia, SC (US)

(72) Inventors: Timothy James Bettles, Columbia, SC (US); Alexander Dobrinsky, Loudonville, NY (US); Michael Shur, Latham, NY (US); Remigijus Gaska, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 14/217,689

(22) Filed: Mar. 18, 2014

(65) Prior Publication Data

US 2014/0264076 A1     Sep. 18, 2014

Related U.S. Application Data

(60) Provisional application No. 61/802,834, filed on Mar. 18, 2013.

(51) Int. Cl.
| | | |
|---|---|---|
| *A61L 2/10* | (2006.01) | |
| *A61L 2/00* | (2006.01) | |
| *A61L 9/00* | (2006.01) | |

(52) U.S. Cl.  
CPC ... *A61L 2/10* (2013.01); *A61L 2/00* (2013.01); *A61L 9/00* (2013.01)

(58) Field of Classification Search  
CPC ................ A61L 2/10; A61L 2/00; A61L 9/00  
USPC ........................................ 250/455.11; 422/24  
See application file for complete search history.

(56) References Cited

U.S. PATENT DOCUMENTS

| 4,806,770 A | 2/1989 | Hylton et al. |
| 6,278,122 B1 | 8/2001 | Gagnon |

(Continued)

FOREIGN PATENT DOCUMENTS

| KR | 20-0370364 Y1 | 12/2004 |
| KR | 10-2012-0066836 A | 6/2012 |

(Continued)

OTHER PUBLICATIONS

Han, PCT Search Report for PCT/US2014/030959, Sep. 5, 2014, 14 pages.

(Continued)

*Primary Examiner* — Nicole Ippolito  
*Assistant Examiner* — Wyatt Stoffa  
(74) *Attorney, Agent, or Firm* — LaBatt, LLC

(57) ABSTRACT

A solution in which an ultraviolet radiation source is mounted on a flexible substrate is provided. The flexible substrate is capable of having a deformation curvature of at least 0.1 inverse meters. The flexible substrate may be incorporated within an existing enclosure or included in the enclosure. The flexible substrate can be utilized as part of a solution for disinfecting one or more items located within the enclosure. In this case, while the items are within the enclosure, ultraviolet radiation is generated and directed at the items. Wiring for the ultraviolet radiation source can be embedded within the flexible substrate and the flexible substrate can have at least one of: a wave-guiding structure, an ultraviolet absorbing surface, or an ultraviolet reflective surface. A control system can be utilized to manage generation of the ultraviolet radiation within the enclosure.

20 Claims, 8 Drawing Sheets

(56) References Cited

U.S. PATENT DOCUMENTS

| | | |
|---|---|---|
| 6,290,713 B1 | 9/2001 | Russell |
| 6,458,331 B1 | 10/2002 | Roberts |
| 6,605,260 B1 | 8/2003 | Busted |
| 6,923,367 B1 | 8/2005 | Grossman et al. |
| 7,372,044 B2 | 5/2008 | Ross |
| 8,318,089 B2 | 11/2012 | Brown-Skrobot et al. |
| 8,330,121 B2 | 12/2012 | Douglas |
| 8,334,521 B2 | 12/2012 | Deshays |
| 8,481,970 B2 | 7/2013 | Cooper et al. |
| 8,899,791 B2* | 12/2014 | Liu .................. 362/249.09 |
| 2005/0254992 A1* | 11/2005 | Jenkins et al. ............ 422/24 |
| 2007/0205382 A1* | 9/2007 | Gaska et al. ............ 250/504 R |
| 2007/0291473 A1* | 12/2007 | Traynor .................. 362/106 |
| 2009/0232701 A1* | 9/2009 | Porat .................... 422/24 |
| 2009/0268461 A1* | 10/2009 | Deak et al. .............. 362/247 |
| 2011/0243789 A1* | 10/2011 | Roberts ................... 422/24 |
| 2012/0018754 A1* | 1/2012 | Lowes .................... 257/98 |
| 2012/0091492 A1* | 4/2012 | Lee et al. ................. 257/98 |
| 2012/0094412 A1* | 4/2012 | Nakamura et al. .......... 438/30 |
| 2012/0165716 A1 | 6/2012 | Reuben |
| 2012/0175667 A1* | 7/2012 | Golle et al. ............... 257/99 |
| 2012/0182755 A1* | 7/2012 | Wildner .................. 362/555 |
| 2014/0034912 A1* | 2/2014 | Liu et al. ................. 257/40 |
| 2014/0183377 A1* | 7/2014 | Bettles et al. ........... 250/455.11 |

FOREIGN PATENT DOCUMENTS

| | | |
|---|---|---|
| KR | 10-2013-0014729 A | 2/2013 |
| WO | 01-14012 A1 | 3/2001 |

OTHER PUBLICATIONS

UV Sterilizer for iPhone, printed from http://www.sinco-elec.com/e_products/Portable-UV-Sterilizer-for-iPhoneiPod-p126.html on Dec. 17, 2013.

Spectroline CB-4000A CellBlaster Operator's Manual, Sep. 2013, 26 pages.

UV Light Sterilizer Cell Phone iPode iPhone ear bud Sanitizer—Keeps Electronic Devices Germ Free!, printed from http://www.ankaka.com/uv-light-sterilizer-cell-phone-ipod-iphone-ear-bud-sanitizer-keeps-electronic-devices-germ-free_p48896.html on Dec. 17, 2013.

* cited by examiner

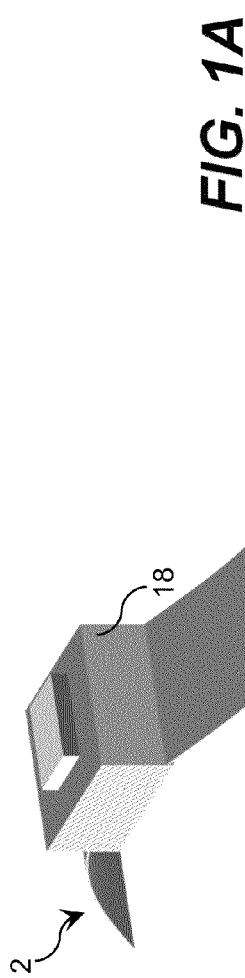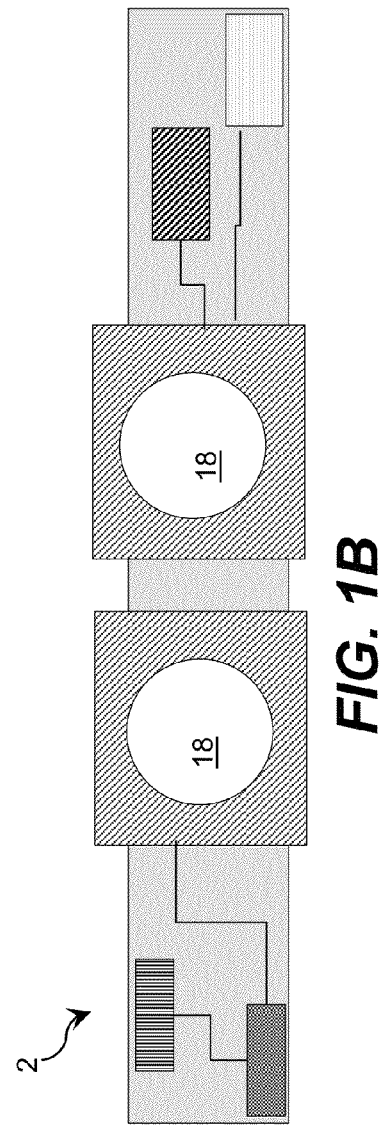

FLEXIBLE ULTRAVIOLET DEVICE

REFERENCE TO RELATED APPLICATION

The current application claims the benefit of U.S. Provisional Application No. 61/802,834, titled "Ultraviolet Light Emitting Device with Flexible Attachment," which was filed on 18 Mar. 2013, and which is hereby incorporated by reference.

TECHNICAL FIELD

The disclosure relates generally to ultraviolet radiation, and more particularly, to a device including a flexible substrate with one or more ultraviolet emitters mounted thereto.

BACKGROUND ART

Ultraviolet (UV) radiation has been utilized to sanitize different devices. For example, there is an approach for sanitizing toothbrushes using UV light. In this approach, an apparatus includes a UV lamp of low intensity for emitting UV radiation in the 200 to 300 nanometer wavelength range, as well as some radiation in the visible range above 300 nanometers and in the ozone producing range below 200 nanometers.

Other sanitizing devices are also known in the art. For example, one approach proposes a mailbox enclosure to sanitize mail articles with UV light and other means. Another approach proposes a surgical tool sterilizing enclosure that utilizes UV light as well as chemical and other sanitizing agents.

Other approaches include a computer input device sterilization apparatus including UV sterilization in an enclosed container to kill bacteria and other disease carrying organisms. One approach includes a horizontal or vertical container dimensioned to fit over computer input devices such as keyboards, mice, trackballs, touchpads and the like. A UV source located within the container irradiates the computer input device with UV light which generates ozone gas, thereby killing any microorganisms that might reside on the computer input device. UV radiation below 200 nm can also be used to create ozone gas having germicidal characteristics. The ozone gas is circulated in and around the input device(s) to provide further sterilization with the UV radiation. A sterilization switch turns the UV source off when the container is opened. A timer/power circuit provides a timed application of power to the UV lamps to provide UV illumination consistent with the substantial sterilization of the input device in question.

There are currently also UV devices available to sterilize mobile phones, such as the UV Sterilizer for the iPhone® from Sinco-Electronic Gifts Co., which is a desktop unit. In this case, a user places his/her phone into the sterilizer for approximately five minutes. The device turns a blue light emitting diode (LED) on to indicate the start of the sterilization process. Once the blue LED turns of, the sterilization process is complete. Such devices typically utilize mercury lamps to generate the ultraviolet light.

SUMMARY OF THE INVENTION

In view of the prior art, the inventors have identified many challenges and limitations of current approaches utilizing ultraviolet radiation, e.g., for disinfecting various commonly used articles. For example, the inventors have noted that current approaches do not utilize and/or are not easily incorporated into existing flexible enclosures.

Embodiments provide a flexible substrate including ultraviolet radiation sources mounted thereto. In an embodiment, a solution provides improved UV LED disinfection of item(s) located within a flexible enclosure. For example, a flexible substrate including ultraviolet radiation sources can be incorporated into such an enclosure. In an illustrative environment, the item(s) within the enclosure can be disinfected by the ultraviolet radiation when the enclosure is closed so that there is no risk that the user of the enclosure could be harmed. In an embodiment, the user can be allowed to carry the enclosure around at any time, while the items within the enclosure are being disinfected.

Aspects of the invention provide an ultraviolet radiation source mounted on a flexible substrate. The flexible substrate is capable of having a deformation curvature of at least 0.1 inverse meters. The flexible substrate may be incorporated within an existing enclosure or included in the enclosure. The flexible substrate can be utilized as part of a solution for disinfecting one or more items located within the enclosure. In this case, while the items are within the enclosure, ultraviolet radiation is generated and directed at the items. Wiring for the ultraviolet radiation source can be embedded within the flexible substrate and the flexible substrate can have at least one of: a wave-guiding structure, an ultraviolet absorbing surface, or an ultraviolet reflective surface. A control system can be utilized to manage generation of the ultraviolet radiation within the enclosure.

A first aspect of the invention provides a system comprising: a flexible substrate capable of having a deformation curvature of at least 0.1 inverse meters; and at least one ultraviolet radiation source mounted on the flexible substrate, the at least one ultraviolet radiation source configured to generate ultraviolet radiation, wherein wiring for the at least one ultraviolet radiation source is embedded within the flexible substrate and the flexible substrate has at least one of: a wave-guiding structure, an ultraviolet absorbing surface, or an ultraviolet reflective surface.

A second aspect of the invention provides an apparatus comprising: an enclosure for containing at least one item for disinfection, wherein at least 5% of an internal surface of the enclosure includes a flexible substrate capable of having a deformation curvature of at least 0.1 inverse meters; and at least one ultraviolet radiation source mounted on the flexible substrate, the at least one ultraviolet radiation source configured to generate ultraviolet radiation within the enclosure, wherein wiring for the at least one ultraviolet radiation source is embedded within the flexible substrate and the flexible substrate has at least one of: a wave-guiding structure, an ultraviolet absorbing surface, or an ultraviolet reflective surface.

A third aspect of the invention provides an apparatus comprising: an enclosure for containing at least one item for disinfection, wherein at least 5% of an internal surface of the enclosure includes a flexible substrate, the flexible substrate capable of having a deformation curvature of at least 0.1 inverse meters; at least one ultraviolet radiation source mounted on the flexible substrate, the at least one ultraviolet radiation source configured to generate ultraviolet radiation within the enclosure; and a control system for managing the ultraviolet radiation generated by the at least one ultraviolet radiation source within the enclosure, wherein wiring for the at least one ultraviolet radiation source and the control system is embedded within the flexible substrate and the flexible substrate has at least one of: a wave-guiding structure, an ultraviolet absorbing surface, or an ultraviolet reflective surface.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 1A shows an isometric view of an illustrative flexible substrate including ultraviolet radiation sources according to an embodiment, while FIG. 1B shows a top view of the illustrative flexible substrate according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 2:
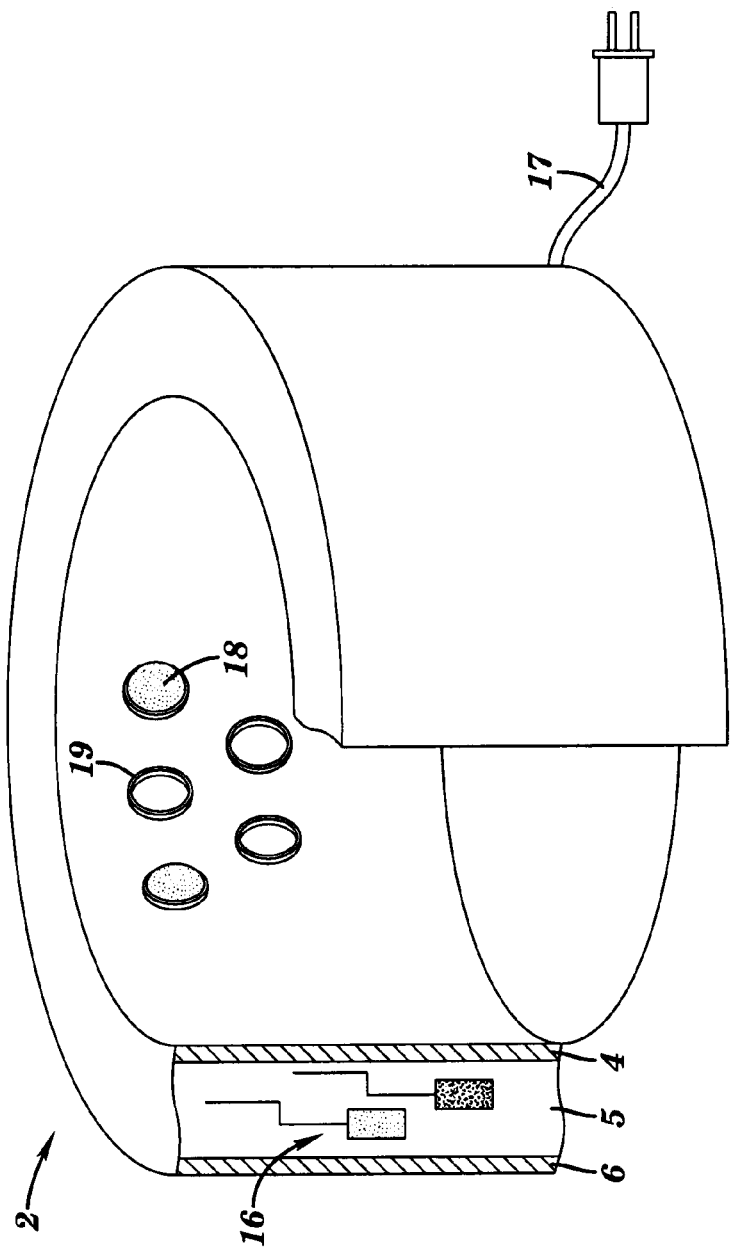
FIG. 2 shows an isometric view of an flexible substrate according to an embodiment.

As indicated above, aspects of the invention provide a solution in which an ultraviolet radiation source is mounted on a flexible substrate. The flexible substrate is capable of having a deformation curvature of at least 0.1 inverse meters. The flexible substrate may be incorporated within an existing enclosure or included in the enclosure. The flexible substrate can be utilized as part of a solution for disinfecting one or more items located within the enclosure. In this case, while the items are within the enclosure, ultraviolet radiation is generated and directed at the items. Wiring for the ultraviolet radiation source can be embedded within the flexible substrate and the flexible substrate can have at least one of: a wave-guiding structure, an ultraviolet absorbing surface, or an ultraviolet reflective surface. A control system can be utilized to manage generation of the ultraviolet radiation within the enclosure.

As used herein, unless otherwise noted, the term "set" means one or more (i.e., at least one) and the phrase "any solution" means any now known or later developed solution. Furthermore, as used herein, ultraviolet radiation/light means electromagnetic radiation having a wavelength ranging from approximately ten nanometers (nm) to approximately four hundred nm, while ultraviolet-C (UV-C) means electromagnetic radiation having a wavelength ranging from approximately one hundred nm to approximately two hundred eighty nm, ultraviolet-B (UV-B) means electromagnetic radiation having a wavelength ranging from approximately two hundred eighty to approximately three hundred fifteen nanometers, and ultraviolet-A (UV-A) means electromagnetic radiation having a wavelength ranging from approximately three hundred fifteen to approximately four hundred nanometers. As also used herein, a material/structure is considered to be "reflective" to ultraviolet light of a particular wavelength when the material/structure has an ultraviolet reflection coefficient of at least thirty percent for the ultraviolet light of the particular wavelength. In a more particular embodiment, a highly ultraviolet reflective material/structure has an ultraviolet reflection coefficient of at least eighty percent. Furthermore, a material/structure is considered to be "transparent" to ultraviolet light of a particular wavelength when the material/structure allows a significant amount of the ultraviolet radiation to pass there through (e.g., at least ten percent of the ultraviolet light radiated at a normal incidence to an interface of the material/structure).

As used herein, the term "disinfection" and its related terms means treating an item so that the item includes a sufficiently low number of contaminants (e.g., chemical) and microorganisms (e.g., virus, bacteria, and/or the like) so that the item can be handled as part of a desired human interaction with no or no reasonable risk for the transmission of a disease or other harm to the human. For example, disinfection of the item means that the item has a sufficiently low level of active microorganisms and/or concentration of other contaminants that a typical human can handle the item without suffering adverse effects from the microorganisms and/or contaminants present on the item. In addition, disinfection can include sterilization. As used herein, the term "sterilization" and its related terms means neutralizing an ability of a microorganism to reproduce, which may be accomplished without physically destroying the microorganism. In this example, a level of microorganisms present on the item cannot increase to a dangerous level and will eventually be reduced, since the replication ability has been neutralized. A target level of microorganisms and/or contaminants can be defined, for example, by a standards setting organization, such as a governmental organization.

Turning to the drawings, FIGS. 1A and 1B show an isometric view and a top view, respectively, of an illustrative flexible substrate 2 according to an embodiment. The flexible substrate 2 can be separate from or incorporated within an enclosure, such as enclosure 14 (FIG. 4), or any of the enclosures in FIGS. 7A-7D. That is, the flexible substrate 2 can be located adjacent to (e.g., mounted on) an interior surface of an existing enclosure, or form a part of the interior surface of an enclosure. In an embodiment, the flexible substrate 2 includes the same material as the enclosure 14. In a more specific embodiment, at least 5% of the internal surfaces of the enclosure 14 can include a flexible material for the flexible substrate 2. The flexible substrate 2 can be formed of any plastic or fabric material capable of including a deformation curvature of at least 0.1 inverse meters. For example, the flexible substrate 2 can be formed of leather, plastic, rubber, cloth, and/or the like. In an embodiment, the flexible substrate 2 can include a flexible printed circuit board.

Ultraviolet radiation source(s) 18 can be mounted on the flexible substrate 2 using any solution. The ultraviolet radiation source(s) 18 can comprise any combination of one or more visible and/or ultraviolet radiation emitters. For example, the ultraviolet radiation source 18 can include a high intensity ultraviolet lamp (e.g., a high intensity mercury lamp), an ultraviolet light emitting diode (LED), super luminescent LEDs, laser diodes, and/or the like. In an embodiment, the ultraviolet radiation source 18 includes a set of light emitting diodes manufactured with one or more layers of materials selected from the group-III nitride material system (e.g., $Al_xIn_yGa_{1-X-Y}N$, where $0 \leq x$, $y \leq 1$, and $x+y \leq 1$ and/or alloys thereof). In an illustrative embodiment, the ultraviolet radiation source 18 can emit ultraviolet radiation in the range of approximately 200 nanometers to approximately 370 nanometers. Additionally, the ultraviolet radiation source 18 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, within the enclosure or at specific items within the enclosure. Illustrative wave guiding structures include, but are not limited to, a plurality of ultraviolet fibers, each of which terminates at an opening, a diffuser, and/or the like.

Turning now to FIG. 2, an isometric view of an illustrative flexible substrate 2 according to an embodiment is shown. The flexible substrate 2 can include a plurality of sockets 19 for the ultraviolet radiation sources 18. The sockets 19 allow for the removal and insertion of the ultraviolet radiation sources 18.

The flexible substrate 2 and/or the enclosure 14 (FIG. 4 and FIGS. 7A-7D) including the flexible substrate 2 can include a plurality of layers for effectively distributing and containing the ultraviolet radiation generated by the ultraviolet radiation source(s) 18. As described herein, the ultraviolet radiation sources 18 mounted on the flexible substrate 2 can include a wave-guiding structure for efficiently directing and delivering the ultraviolet radiation. Additionally, the flexible substrate 2 can include a reflective layer 4 configured to reflect and recycle the ultraviolet radiation within the enclosure. The reflective layer 4 can include a material having a low refractive index, such as aluminum (highly polished), and/or the like, for total internal reflection. The flexible substrate 2 can also include a padding layer 5 for containing, for example, one or more electronic components of a control system (e.g., control system 16 in FIG. 5) for managing operation of the ultraviolet radiation source(s) 18. Examples of materials for the padding layer 5 include insulating rubber material, flexible plastic, and/or the like. An ultraviolet radiation absorbent layer 6 also can be included in the flexible substrate 2 and be configured to prevent ultraviolet radiation from exiting an enclosure. The ultraviolet radiation absorbent layer 6 can include any material capable of absorbing ultraviolet radiation to prevent a user from being harmed by the ultraviolet radiation. For example, the ultraviolet radiation absorbent layer 6 can be formed of polycarbonate, a transparent thermoplastic (e.g., Plexiglas), polyethylene, and/or the like.

Figure 3:
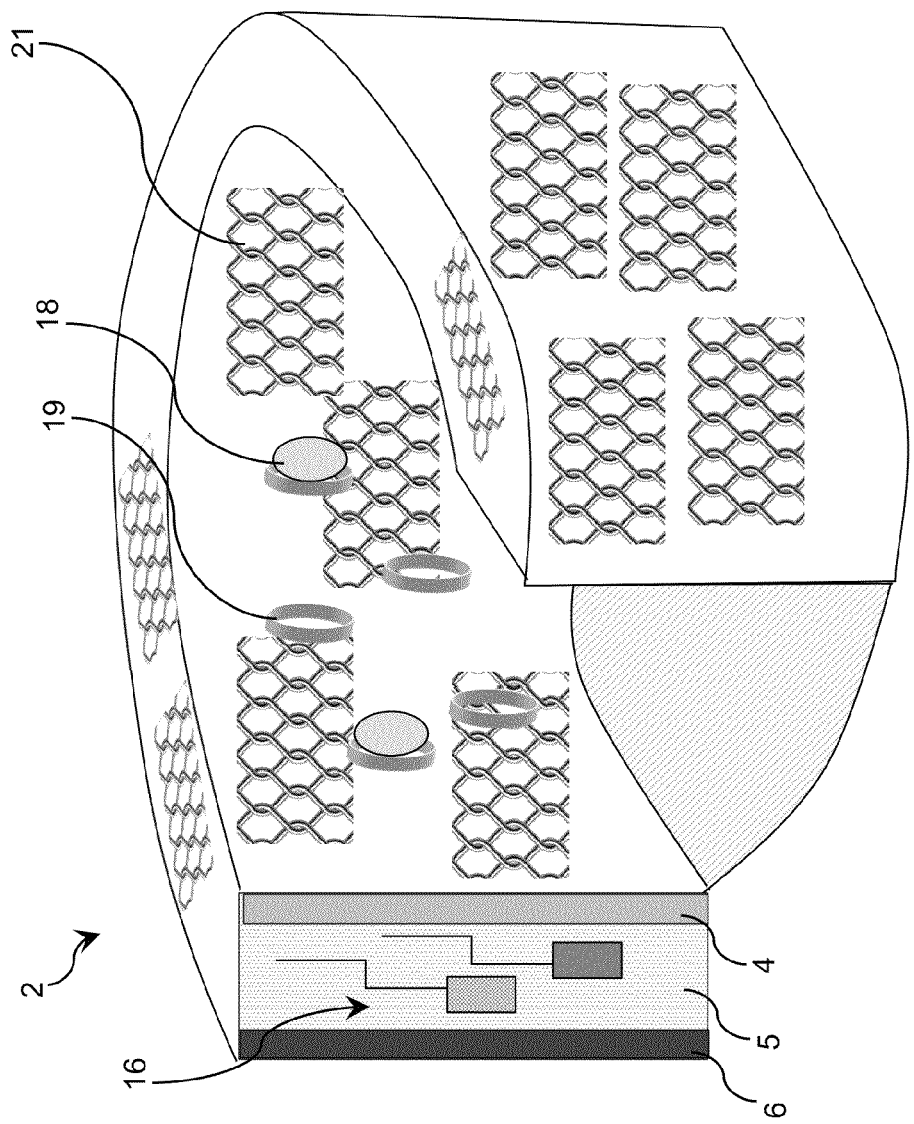
FIG. 3 shows an isometric view of an flexible substrate according to an embodiment.

In an embodiment, as shown in FIG. 3, the flexible substrate 2 can include a multi-dimensional inner wire layer 21 extending across substantially all of the height and width of the flexible substrate 2. The inner wire layer 21 can be incorporated into any layer of the flexible substrate 2, such as the reflective layer 4 and/or the padding layer 5. The inner wire layer 21 can be configured in any pattern, such as the mesh pattern shown in the figure. During and/or just prior to operation of the ultraviolet radiation sources 18, a control system can generate and monitor a low electrical current through the inner mesh wire layer 21. In an embodiment, the control system can utilize the current generated in the inner mesh wire layer 21 to determine if the flexible substrate 2, e.g., as part of an exterior side of the enclosure 14, has been punctured or torn. For example, if the enclosure is punctured or torn, the inner mesh wire layer 21 also will be punctured, causing a change (e.g., an increase) in the electrical current of the inner mesh wire layer 21. The control system can detect the change and, in response, turn off or not turn on the ultraviolet radiation sources 18.

Figure 4:
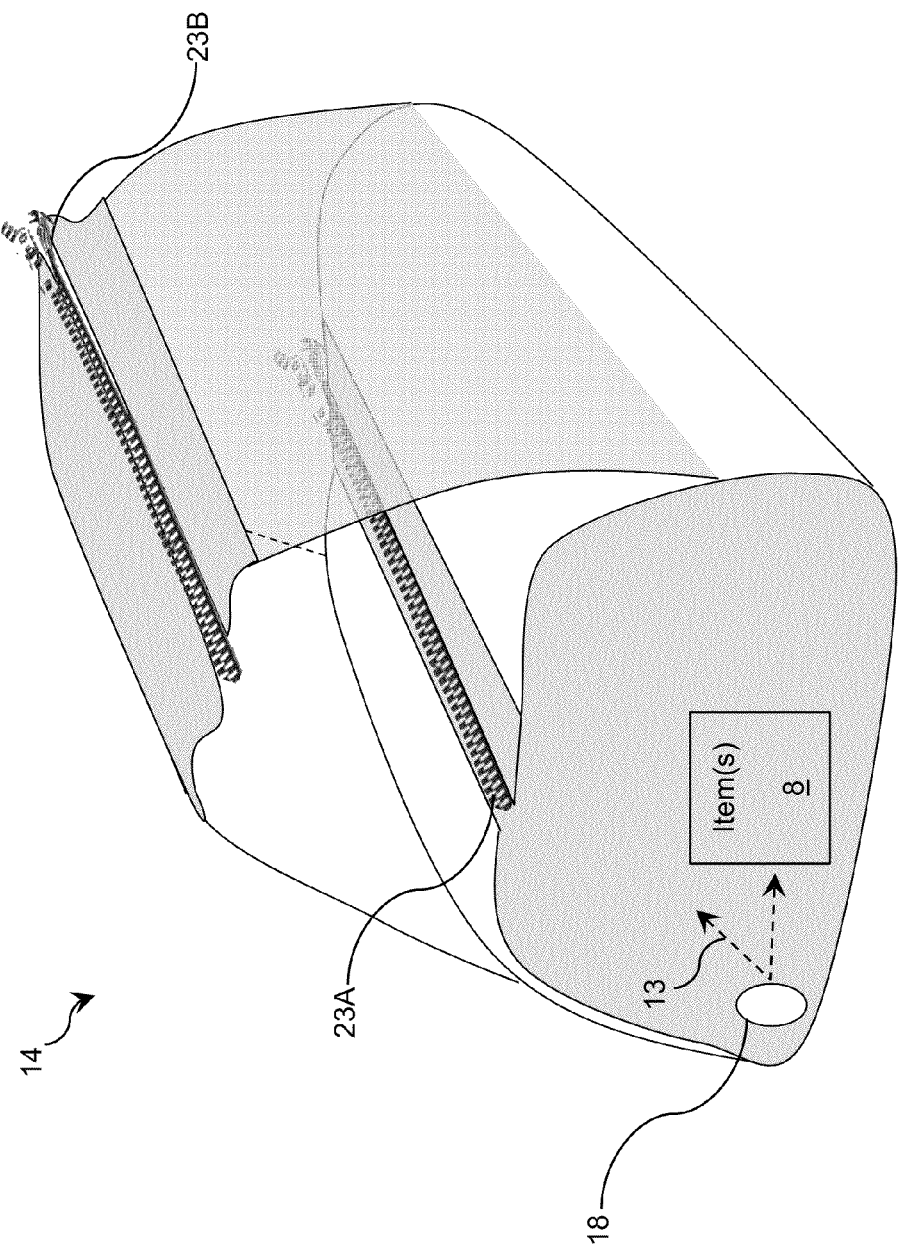
FIG. 4 shows an isometric view of an enclosure according to an embodiment.

In an embodiment, as shown in FIG. 4, an enclosure 14 can include multiple closing mechanisms. For example, enclosure 14 can comprise a double closing mechanism, including a first closure mechanism 23A and a second closure mechanism 23B. The first closure mechanism 23A can be a first ultraviolet absorbent zipper and the second closure mechanism 23B can be a second ultraviolet absorbent zipper. Although only two closure mechanisms are shown, it is understood that multiple closures can be provided for the enclosure 14 to ensure that the enclosure 14 is well sealed and a user cannot be harmed by the ultraviolet radiation. Furthermore, although FIG. 4 shows the first closure mechanism 23A and the second closure mechanism 23B as zippers, it is understood that any closure mechanism can be provided. For example, one or more of the closures can include Velcro, and/or the like. In an embodiment, the first enclosure mechanism 23A encloses a portion of the enclosure 14 that includes the item(s) 8 and the ultraviolet radiation source(s) 18. The second enclosure mechanism 23B, and any other enclosure mechanisms that are included, ensure that the enclosure 14 is well sealed and protect the user from the ultraviolet radiation. In an embodiment, the control system can monitor the closure mechanisms 23A, 23B. In response to at least one of the closure mechanisms 23A, 23B being open, the control system can turn off or not turn on the ultraviolet radiation source(s) 18.

Although not shown, in an embodiment, the enclosure 14 can include a material with antibacterial properties that are activated by radiation. The material can coat some or all of an interior surface of the enclosure. For example, some or all of an interior surface of the enclosure 14 can include indocyanine green, which is activated by radiation with 808 nm wavelength. Other materials with antibacterial properties can include copper and its alloys.

Figure 5:
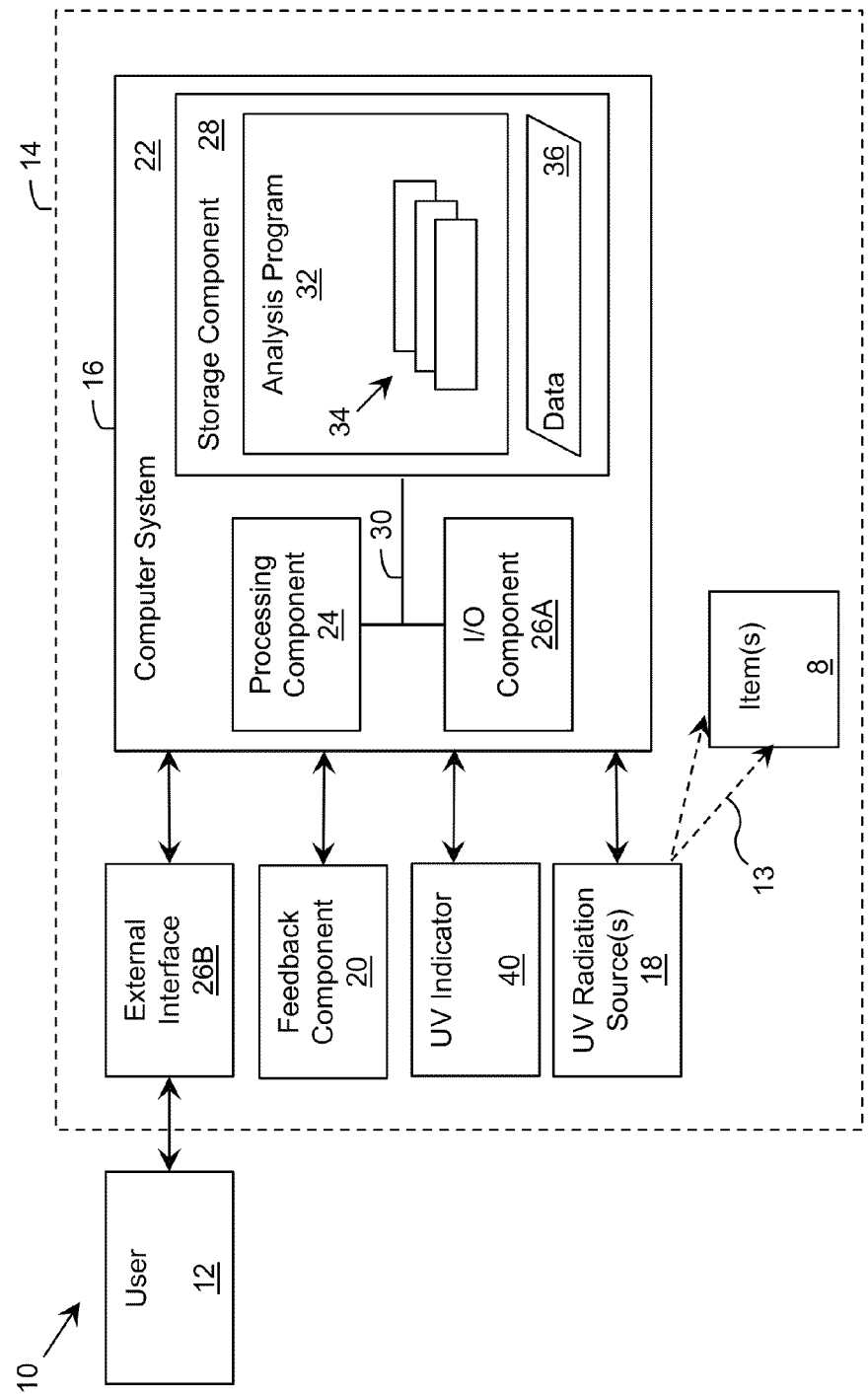
FIG. 5 shows an illustrative ultraviolet radiation system for an enclosure according to an embodiment.

Turning now to FIG. 5, an illustrative ultraviolet radiation system 10 according to an embodiment is shown. In this case, the system 10 includes a monitoring and/or control system 16, which can be incorporated into the flexible substrate 2 (FIG. 2). For example, the monitoring and/or control system 16 can be embedded on a wall forming an ultraviolet absorbent case 14. The monitoring and/or control system 16 is shown implemented as a computer system 22 including an analysis program 32, which makes the computer system 22 operable to manage a set of ultraviolet radiation sources 18 (mounted on a flexible substrate 2) by performing a process described herein. In particular, the analysis program 32 can enable the computer system 22 to operate the set of ultraviolet radiation sources 18 to generate and direct ultraviolet radiation within the enclosure 14 and process data 36 corresponding to one or more attributes within the enclosure 14 and/or one or more attributes of the enclosure (e.g., opened/closed, punctured, and/or the like), which are acquired by a feedback component 20. While a single ultraviolet radiation source 18 is shown in this figure, it is understood that the enclosure 14 can include any number of ultraviolet radiation sources 18 (e.g., mounted on the flexible substrate 2 incorporated with the enclosure 14 or a part of the enclosure 14), the operation of which the computer system 22 can separately manage using a process described herein. In the case of more than one ultraviolet radiation source 18, it is understood that the computer system 22 can individually control each ultraviolet radiation source 18 and/or control two or more of the ultraviolet radiation sources 18 as a group. Furthermore, while ultraviolet radiation sources 18 are described herein, it is understood that the monitoring and/or control system 16 can operate one or more other types of devices, such as visible light LEDs, and/or the like.

In an embodiment, during an initial period of operation (e.g., after an item 8 is placed within the enclosure 14 and the enclosure 14 is closed, and/or the like), the computer system 22 can acquire data from the feedback component 20 regarding one or more attributes within the enclosure 14 and generate data 36 for further processing. The data 36 can include a presence of biological activity (e.g., microorganisms, viruses, bacteria, and/or the like) on a surface of one or more items 8 or within the enclosure 14, a disinfection schedule history for the enclosure 14, a determination of whether the enclosure 14 is closed or open, and/or the like. The item(s) 8 can include any personal item that a user 12 desires to be disinfected. For example, illustrative items 8 can include food items, toiletries, cosmetics, liquids, fitness clothing/equipment, small electronic gadgets, and/or the like. The computer system 22 can use the data 36 to control one or more aspects of the ultraviolet radiation generated by the ultraviolet radiation source(s) 18.

Furthermore, one or more aspects of the operation of the ultraviolet radiation source 18 can be controlled by a user 12 via an external interface component 26B. The external interface component 26B can be located on an exterior portion of the enclosure 14 and allow the user 12 to choose when to turn on the ultraviolet radiation source 18. However, it is understood that the monitoring and/or control system 16 (e.g., via the wiring described herein and/or a sensor and/or switch 38 shown in FIG. 6) must still determine that the enclosure 14 is closed and/or not punctured prior to turning on the ultraviolet radiation source 18 to avoid harming the user 12. The external interface component 26B can include a touch screen that shows control dials for adjusting an intensity, scheduling, and other operational properties of the at least one ultraviolet radiation source 18. In an embodiment, the external interface component 26B can include a touchscreen, a keyboard, a plurality of buttons, a joystick-like control mechanism, and/or the like, to control the at least one ultraviolet radiation source 18. In an alternative embodiment, the external interface component 26B can be separate from the enclosure 14. For example, the external interface component 26B can include a remote or a mobile device including a software installed on the operating system thereon, to control the ultraviolet radiation source(s) 18. Such a component 26B can communicate with the remaining portions of the control system 16 wirelessly, via Wi-Fi, Bluetooth, and/or the like. In an illustrative embodiment, the external interface component 26B comprises a personal mobile device, such as a mobile phone, or the like, which includes an ability (e.g., via a mobile app installed thereon) to communicate with the control system 16 using a wireless communications solution.

The computer system 22 is shown including a processing component 24 (e.g., one or more processors), a storage component 28 (e.g., a storage hierarchy), an input/output (I/O) component 26A (e.g., one or more I/O interfaces and/or devices), and a communications pathway 30. In general, the processing component 24 executes program code, such as the analysis program 32, which is at least partially fixed in the storage component 28. While executing program code, the processing component 24 can process data, which can result in reading and/or writing transformed data from/to the storage component 28 and/or the I/O component 26A for further processing. The pathway 30 provides a communications link between each of the components in the computer system 22. The I/O component 26A and/or the external interface component 26B can comprise one or more human I/O devices, which enable a human user 12 to interact with the computer system 22 and/or one or more communications devices to enable a system user 12 to communicate with the computer system 22 using any type of communications link. To this extent, during execution by the computer system 22, the analysis program 32 can manage a set of interfaces (e.g., graphical user interface(s), application program interface, and/or the like) that enable human and/or system users 12 to interact with the analysis program 32. Furthermore, the analysis program 32 can manage (e.g., store, retrieve, create, manipulate, organize, present, etc.) the data, such as data 36, using any solution.

In any event, the computer system 22 can comprise one or more general purpose computing articles of manufacture (e.g., computing devices) capable of executing program code, such as the analysis program 32, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 32 can be embodied as any combination of system software and/or application software.

Furthermore, the analysis program 32 can be implemented using a set of modules 34. In this case, a module 34 can enable the computer system 22 to perform a set of tasks used by the analysis program 32, and can be separately developed and/or implemented apart from other portions of the analysis program 32. When the computer system 22 comprises multiple computing devices, each computing device can have only a portion of the analysis program 32 fixed thereon (e.g., one or more modules 34). However, it is understood that the computer system 22 and the analysis program 32 are only representative of various possible equivalent monitoring and/or control systems 16 that may perform a process described herein. To this extent, in other embodiments, the functionality provided by the computer system 22 and the analysis program 32 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 16 can be implemented without any computing device, e.g., using a closed loop circuit implementing a feedback control loop in which the outputs of one or more sensing devices are used as inputs to control the operation of one or more other devices (e.g., LEDs). Illustrative aspects of the invention are further described in conjunction with the computer system 22. However, it is understood that the functionality described in conjunction therewith can be implemented by any type of monitoring and/or control system 16.

Regardless, when the computer system 22 includes multiple computing devices, the computing devices can communicate over any type of communications link. Furthermore, while performing a process described herein, the computer system 22 can communicate with one or more other computer systems, such as the user 12, using any type of communications link. In either case, the communications link can comprise any combination of various types of wired and/or wireless links; comprise any combination of one or more types of networks; and/or utilize any combination of various types of transmission techniques and protocols.

The system 10 also can include an ultraviolet radiation indicator 40 (e.g., an LED), which can be operated by the computer system 22 to indicate when ultraviolet radiation is being generated and directed within the enclosure 14. The ultraviolet radiation indicator 40 can include one or more LEDs for emitting a visual light for the user 12. In another embodiment, the ultraviolet radiation indicator 40 can include a sound or a vibration for a predetermined amount of time to indicate that ultraviolet radiation is being and/or is no longer being generated within the enclosure 14.

Figure 6:
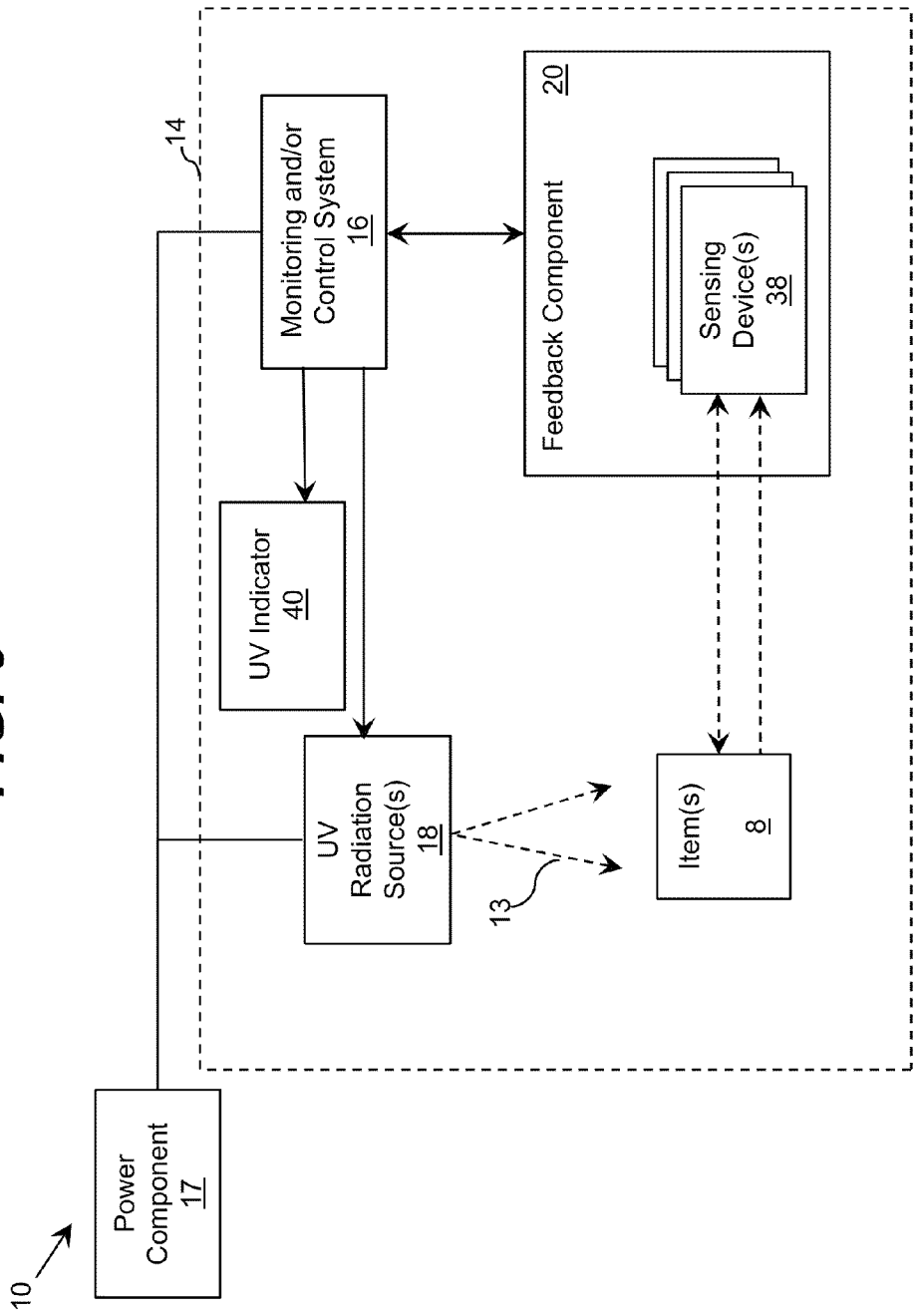
FIG. 6 shows an illustrative system including an ultraviolet radiation system for an enclosure according to an embodiment.

Turning now to FIG. 6, an illustrative system including an ultraviolet radiation system 10 for the enclosure 14 is shown. The ultraviolet radiation system 10 is shown including ultraviolet radiation source(s) 18 (mounted on a flexible substrate 2 as shown in FIG. 1). The monitoring and/or control system 16 is configured to control the ultraviolet radiation source(s) 18 to direct ultraviolet radiation 13 within the enclosure 14 and at item(s) 8 located within the enclosure 14. The feedback component 20 is configured to acquire attribute data used by the monitoring and/or control system 16 to manage the ultraviolet radiation source(s) 18. As illustrated, the feedback component 20 can include a plurality of sensing devices 38, each of which can acquire attribute data used by the monitoring and/or control system 16 to control and manage the ultraviolet radiation source(s) 18.

The attribute data acquired by the feedback component 20 can include any combination of a plurality of attributes of the enclosure 14 and/or item(s) 8 located therein. Illustrative attributes for the enclosure 14 can include: a presence of biological activity within the enclosure 14 or on items 8 within the enclosure 14, a determination of whether the enclosure 14 is open or closed, a determination of whether the enclosure 14 is punctured or torn, and/or the like. A sensing device 38 can include a sensor and/or a switch 38 to sense that an opening of the enclosure 14 is physically closed before the monitoring and/or control system 16 turns on the ultraviolet radiation source(s) 18. Furthermore, the sensing device 38 can sense that biological activity is present within the enclosure 14 before the monitoring and/or control system 16 turns on the ultraviolet radiation source(s) 18.

In the case of determining a presence of biological activity on the item(s) 8, the sensing devices 38 can also determine a location of the biological activity, a type of biological activity (e.g., type of organism), a concentration of the biological activity, an estimated amount of time an organism has been in a growth phase (e.g., exponential growth and/or stationary), and/or the like. Furthermore, the sensing device 38 can determine information on the variation of the biological activity over time, such as a growth rate, a rate with which an area including the biological activity is spreading, and/or the like. In an embodiment, a set of biological activity dynamics are related to various attributes of bacteria and/or virus activity within the enclosure 14 and/or on an item 8, including, for example, the presence of detectable bacteria and/or virus activity, measured bacteria and/or virus population/concentration time dynamics, growth phase, and/or the like.

In an embodiment, to determine the presence of biological activity within the enclosure 14, the sensing devices 38 include at least one of a visual camera or a chemical sensor. The visual camera can acquire visual data (e.g., visual, electronic, and/or the like) used to monitor the enclosure 14, while the chemical sensor can acquire chemical data (e.g., chemical, electronic, and/or the like) used to monitor the enclosure 14. For example, when the monitoring and/or control system 16 is operating the ultraviolet radiation source 18, a visual camera and/or a chemical sensor 38 monitoring an interior of the enclosure 14 may be operated to detect the presence of microorganisms. In a specific embodiment, the visual camera 38 comprises a fluorescent optical camera that can detect bacteria and/or viruses that become fluorescent under ultraviolet radiation. However, it is understood that a visual camera and a chemical sensor are only illustrative of various types of sensors that can be implemented. For example, the sensing devices 38 can include one or more mechanical sensors (including piezoelectric sensors, various membranes, cantilevers, a micro-electromechanical sensor or MEMS, a nanomechanical sensor, and/or the like), which can be configured to acquire any of various types of data regarding the enclosure 14.

The monitoring and/or control system 16 can be configured to control and adjust a direction, an intensity, a pattern, and/or a spectral power (e.g., wavelength) of the at least one ultraviolet radiation source 18, based on attribute data acquired by the feedback component 20. The monitoring and/or control system 16 can control and adjust each property of the ultraviolet radiation source 18 independently. For example, the monitoring and/or control system 16 can adjust the intensity, time duration, and/or time scheduling (e.g., including duration (e.g., exposure/illumination time)), duty cycle, time between exposures/illuminations, and/or the like) of the ultraviolet radiation source 18 for a given wavelength. Each of the properties of the ultraviolet radiation source 18 can be adjustable and controlled by the monitoring and/or control system 16 according to data provided by the feedback component 20. In another embodiment, when the enclosure includes multiple compartments, such as the example shown in FIG. 7C, the monitoring and/or control system 16 can be configured to control the ultraviolet radiation sources 18 in each compartment autonomously from other compartments. For example, if the enclosure 14 includes a plurality of compartments for different food items, the monitoring and/or control system 16 can be configured to control and adjust the ultraviolet radiation source(s) 18 in each compartment according to the food items within the respective compartment.

The monitoring and/or control system 16 can also be configured to adjust the direction of the ultraviolet radiation according to a location of the biological activity detected within the enclosure 14 by the sensing device(s) 38 using any solution. The monitoring and/or control system 16 can be configured to utilize a target timing, intensity, and/or spectral power of the ultraviolet radiation according to a type of biological activity. That is, the sensing devices 38 can sense locations of higher levels of biological activity on specific items 8 within the enclosure 14, and the ultraviolet radiation source 18 can be configured by the monitoring and/or control system 16 to direct higher doses (by increasing intensity or exposure) of ultraviolet radiation at the item(s) 8 with higher levels of biological activity (e.g., non-uniform ultraviolet radiation).

The sensing devices 38 can also sense that the enclosure 14 is physically open or closed. In response to detecting that the enclosure 14 is closed, the monitoring and/or control system 16 can be configured to automatically turn on the ultraviolet radiation. In one embodiment, the monitoring and/or control system 16 can be configured to set a periodic or an aperiodic schedule for the ultraviolet radiation when the enclosure 14 is closed. This (periodic or aperiodic) schedule can be interrupted when the sensing device 38 senses that the enclosure 14 is opened and the monitoring and/or control system 16 can be configured to turn off the ultraviolet radiation. In this case, the schedule (periodic or aperiodic) can be resumed once the sensing device 38 senses the enclosure 14 is closed again. For example, in the embodiment of the enclosure 14 shown in FIG. 4, if the sensing device 38 senses that the second closure mechanism 23B is open, the monitoring and/or control system 16 can be configured to turn off the ultraviolet radiation. Once the second closure mechanism 23B is closed, the monitoring and/or control system 16 can be configured to turn on the ultraviolet radiation and resume the disinfecting of the enclosure 14 and the item(s) 8 located therein.

The sensing device 38 can also sense whether the enclosure 14 is punctured or torn. In the embodiment of the enclosure 14 including the multi-dimensional inner wire layer 21 (FIG. 3), the sensing device 38 can continuously monitor the electrical current of the inner wire layer 21. In an embodiment, the monitoring and/or control system 16 can be configured to determine whether the electrical current of the inner wire layer 21 is unexpectedly changed (e.g., increased). In response to such a change in the electrical current of the inner wire layer 21, the monitoring and/or control system 16 can determine that there is a puncture or tear in the enclosure 14 that could allow ultraviolet radiation to escape. In response, the monitoring and/or control system 16 can turn off the ultraviolet radiation sources 18 so that the user 12 is not harmed.

It is understood that the system 10 may include a power component 17 to supply power to one or more of the various components of system 10, such as ultraviolet radiation sources 18, feedback component 20, monitoring and/or control system 16, and/or the like. The power component 17 can be separate from the enclosure 14 (e.g., an electrical cord enabling power to be obtained via an electric grid (e.g., a household outlet), as seen in FIG. 2), or include be included with the enclosure 14 (e.g., rechargeable batteries). The power component 17 can comprise any source of power including, but not limited to, a battery set, a solar cell, another electronic device (e.g., via a universal serial bus (USB) connection), and/or the like. For example, the power component 17 can include any of various types of rechargeable batteries (e.g., lithium ion, nickel-cadmium, and/or the like). The power component 17 can be configured for operation of high efficiency direct current (DC) step-up/boost converters. In an embodiment, the power component (e.g., conversion efficiency and maximum battery life) is configured (e.g., optimized) to keep a difference between the electrical power available versus the electrical power required for the various components at the minimum. In an embodiment, the power component comprises a battery set that is capable of being recharged through a typical household outlet. A charging system for this embodiment can comprise an electrical cord for charging that can include, for example, a cord with a USB connection, which can enable charging and communications with an external computing device.

For each embodiment of the enclosure 14 including the ultraviolet radiation source(s) 18 (mounted on the flexible substrate 2), the enclosure 14 can be configured to provide at least a target amount of mechanical protection for the item(s) 8 located within the enclosure 14. For example, the target amount of mechanical protection can provide at least ten feet drop protection for the items 8 located within the enclosure 14, which can be measured by a drop test. The drop test can include dropping the enclosure from a height of approximately ten feet. This drop test can be performed multiple times, while capturing images of the landing each time. The items 8 within the enclosure 14 can be examined after each drop to ensure the no significant damage has occurred. In an embodiment, portions of an exterior of the enclosure 14 can include a material that absorbs the impact from the drop. For instance, portions of the exterior of the enclosure 14 can be made of rubber or plastic. Additionally, the material can rubberized polycarbonate, polycarbonate, an acrylonitrile butadiene styrene (ABS) composite, polyurethane composites, and/or the like.

For each embodiment of the enclosure 14, a layer of the enclosure 14 can be configured to include waterproof material. For example, the enclosure 14 can be configured to store liquids and the control system can be used to manage ultraviolet radiation sources for disinfecting the liquids. The waterproof material can comprise rubber, fluorinated ethylene propylene (FEP), polytetrafluoroethylene (PTFE, such as Teflon), ultraviolet resistant polycarbonate, an ultraviolet resistant transparent thermoplastic, and/or the like. The waterproof layer can be configured to prevent the liquids from exiting the enclosure 14 and also from affecting any of the electrical components of the system 10 (e.g., ultraviolet radiation sources 18, the computer system 22, and/or the like).

Figure 7A:
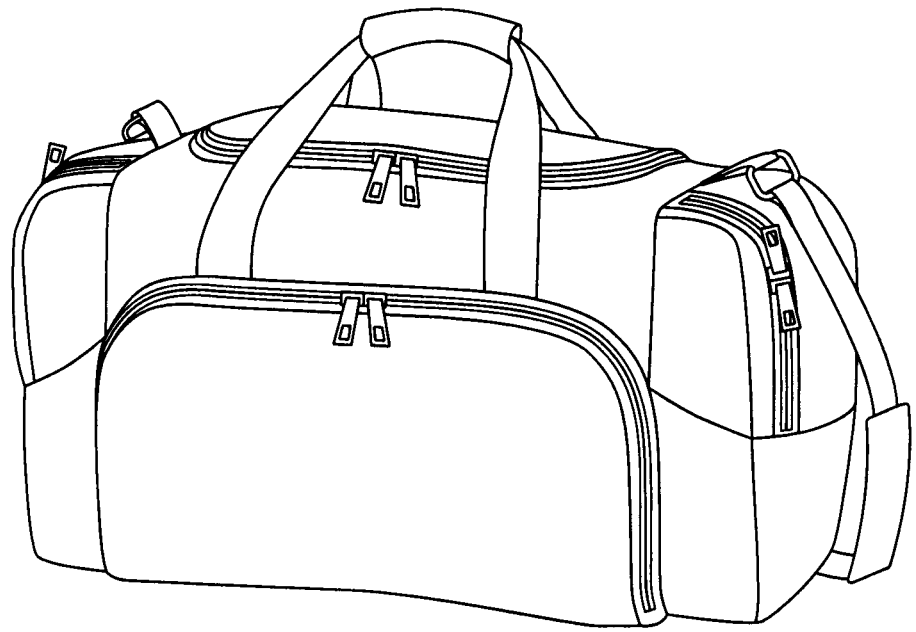
FIGS. 7A-7D show illustrative enclosures for use with an ultraviolet radiation system according to an embodiment.
Figure 7B:
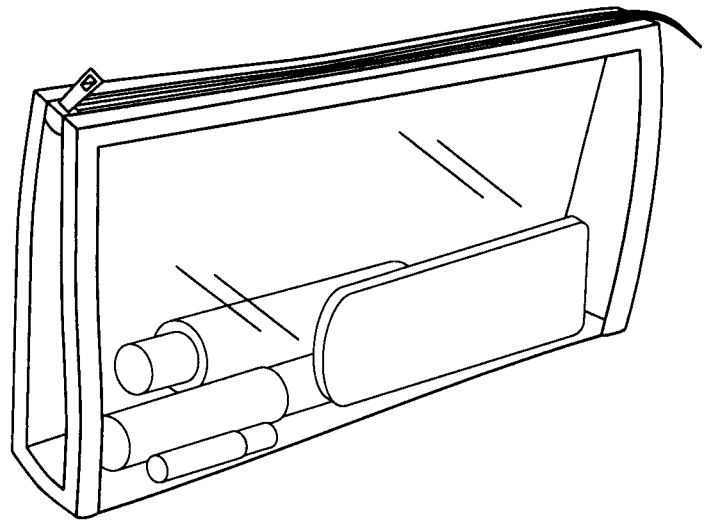
Figure 7C:
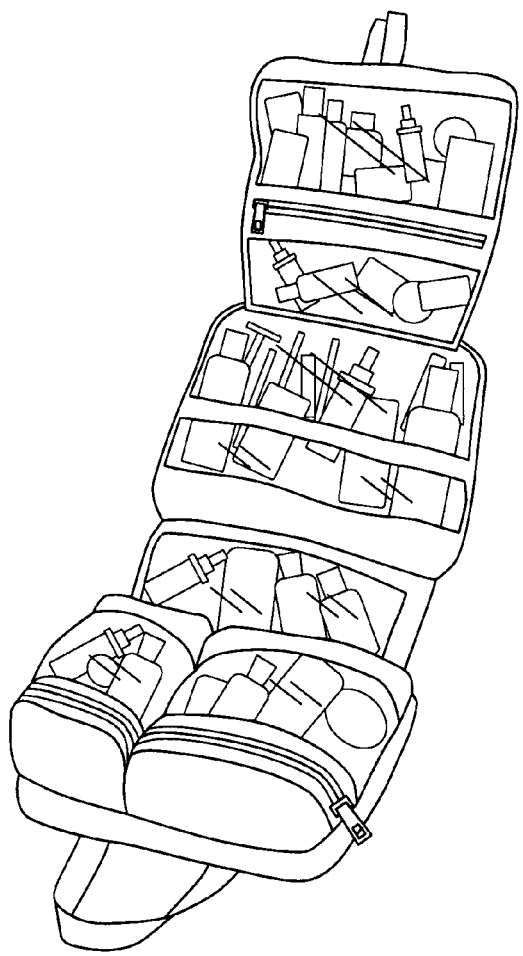
Figure 7D:
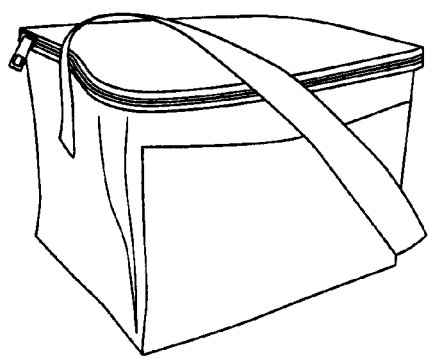

As described herein, embodiments can be implemented as part of any type of enclosure 14. FIGS. 7A-7D show illustrative enclosures for use with an ultraviolet radiation system 10 (FIG. 5) according to embodiments. For example, the enclosure can be a duffle bag (FIG. 7A) for storing a plurality of clothes or personal items. Alternatively, the enclosure can be a small cosmetic bag (FIG. 7B). The enclosure can be toiletry bag with multiple compartments (FIG. 7C), a lunch box (FIG. 7D), and/or the like. In each case, an embodiment of the system 10 can be implemented in conjunction therewith using any solution. To this extent, it is understood that embodiments of the system 10 can vary significantly in the number of devices, the size of the devices, the power requirements for the system, and/or the like. Regardless, it is understood that these are only exemplary enclosures and that the system 10 may be applicable to other enclosures not specifically mentioned herein.

While shown and described herein as a method and system for disinfecting items located within a flexible enclosure, it is understood that aspects of the invention further provide various alternative embodiments. For example, in one embodiment, the invention provides a computer program fixed in at least one computer-readable medium, which when executed, enables a computer system to disinfect the flexible enclosure and/or items located within the flexible enclosure using a process described herein. To this extent, the computer-readable medium includes program code, such as the analysis program 32 (FIG. 5), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the analysis program 32 (FIG. 5), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for disinfecting a flexible enclosure and/or items within the flexible enclosure. In this case, the generating can include configuring a computer system, such as the computer system 22 (FIG. 5), to implement a method of disinfecting the flexible enclosure and/or items within the flexible enclosure as described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
    a flexible substrate capable of having a deformation curvature of at least 0.1 inverse meters, wherein the flexible substrate forms an enclosure having a sealable opening; and
    at least one ultraviolet radiation source mounted on the flexible substrate, the at least one ultraviolet radiation source configured to generate ultraviolet radiation,
    wherein wiring for the at least one ultraviolet radiation source is embedded within the flexible substrate and the flexible substrate has a wave-guiding structure and a plurality of layers for distributing and containing the ultraviolet radiation within the enclosure, the plurality of layers including: an ultraviolet reflective surface on an interior surface of the enclosure, a padding layer adjacent to the ultraviolet reflective surface, and an ultraviolet absorbing surface adjacent to the padding layer, wherein the ultraviolet radiation is directed toward an interior of the enclosure.

2. The system of claim 1, wherein the flexible substrate includes a flexible printed circuit board.

3. The system of claim 1, further comprising a control system for managing the ultraviolet radiation generated by the at least one ultraviolet radiation source.

4. The system of claim 3, wherein the control system is mounted on the flexible substrate.

5. The system of claim 3, wherein managing includes:
    monitoring an electrical current in the wiring during operation of the at least one ultraviolet radiation source; and
    turning off the at least one ultraviolet radiation source in response to detecting an increase in the electrical current.

6. An apparatus comprising:
    an enclosure having a sealable opening for containing at least one item for disinfection, wherein at least 5% of an internal surface of the enclosure includes a flexible substrate capable of having a deformation curvature of at least 0.1 inverse meters; and
    at least one ultraviolet radiation source mounted on the flexible substrate, the at least one ultraviolet radiation source configured to generate ultraviolet radiation within the enclosure,
    wherein wiring for the at least one ultraviolet radiation source is embedded within the flexible substrate and the flexible substrate has a wave-guiding structure and a plurality of layers for distributing and containing the ultraviolet radiation within the enclosure, the plurality of layers including: an ultraviolet reflective surface on an interior surface of the enclosure, a padding layer adjacent to the ultraviolet reflective surface, and an ultraviolet absorbing surface adjacent to the padding layer.

7. The apparatus of claim 6, wherein the flexible substrate includes a flexible printed circuit board.

8. The apparatus of claim 6, further comprising a control system for managing the ultraviolet radiation generated by the at least one ultraviolet radiation source.

9. The apparatus of claim 8, wherein the flexible substrate includes a flexible printed circuit board, and wherein the control system is mounted on the flexible substrate.

10. The apparatus of claim 8, wherein the enclosure comprises a double closing mechanism configured to prevent the ultraviolet radiation from exiting the enclosure.

11. The apparatus of claim 10, wherein the managing comprises:
    determining an outer closure mechanism is open; and
    turning off the at least one ultraviolet radiation source in response to the determining.

12. The apparatus of claim 8, wherein the managing includes:
    monitoring an electrical current in the wiring during operation of the at least one ultraviolet radiation source; and
    turning off the at least one ultraviolet radiation source in response to detecting an increase in the electrical current.

13. The apparatus of claim 6, wherein the enclosure is waterproof.

14. The apparatus of claim 6, further comprising an antibacterial material located within the enclosure, wherein the antibacterial material is activated by the ultraviolet radiation.

15. An apparatus comprising:
    an enclosure having a sealable opening for containing at least one item for disinfection, wherein at least 5% of an internal surface of the enclosure includes a flexible substrate, the flexible substrate capable of having a deformation curvature of at least 0.1 inverse meters;
    at least one ultraviolet radiation source mounted on the flexible substrate, the at least one ultraviolet radiation source configured to generate ultraviolet radiation within the enclosure; and
    a control system for managing the ultraviolet radiation generated by the at least one ultraviolet radiation source within the enclosure,
    wherein wiring for the at least one ultraviolet radiation source is embedded within the flexible substrate and the flexible substrate has a wave-guiding structure and a plurality of layers for distributing and containing the ultraviolet radiation within the enclosure, the plurality of layers including: an ultraviolet reflective surface on an interior surface of the enclosure, a padding layer adjacent to the ultraviolet reflective surface, and an ultraviolet absorbing surface adjacent to the padding layer.

16. The apparatus of claim 15, wherein the enclosure comprises a plurality of compartments and each compartment includes at least one ultraviolet radiation source.

17. The apparatus of claim 16, wherein the managing includes separately and independently controlling the at least one ultraviolet radiation source in each compartment.

18. The apparatus of claim 16, wherein each compartment is configured to contain a different food item for disinfection.

19. The apparatus of claim 15, wherein the managing includes:
- monitoring an electrical current in the wiring during operation of the at least one ultraviolet radiation source; and
- turning off the at least one ultraviolet radiation source in response to detecting an increase in the electrical current.

20. The apparatus of claim 15, wherein the flexible substrate includes a flexible printed circuit board.

\* \* \* \* \*